United States Patent
Killip (10) Patent No.: US 10,487,954 B2
(45) Date of Patent: Nov. 26, 2019

(54) BLEND VALVE

(71) Applicant: Micromeritics Instrument Corporation, Norcross, GA (US)

(72) Inventor: Graham Robert Killip, Alpharetta, GA (US)

(73) Assignee: Micromeritics Instrument Corporation, Norcross, GA (US)

( * ) Notice: Subject to any disclaimer, the term of this patent is extended or adjusted under 35 U.S.C. 154(b) by 10 days.

(21) Appl. No.: 15/877,679

(22) Filed: Jan. 23, 2018

(65) Prior Publication Data

US 2018/0224006 A1    Aug. 9, 2018

Related U.S. Application Data

(60) Provisional application No. 62/454,503, filed on Feb. 3, 2017.

(51) Int. Cl.
| | |
|---|---|
| *F16K 11/074* | (2006.01) |
| *G01N 30/38* | (2006.01) |
| *G01N 30/20* | (2006.01) |
| *G01N 30/34* | (2006.01) |

(52) U.S. Cl.
CPC .......... *F16K 11/0743* (2013.01); *G01N 30/20* (2013.01); *G01N 30/38* (2013.01); *G01N 30/34* (2013.01); *G01N 2030/201* (2013.01); *G01N 2030/347* (2013.01); *Y10T 137/86823* (2015.04); *Y10T 137/87249* (2015.04)

(58) Field of Classification Search
CPC ..... Y10T 137/86823; Y10T 137/87249; F16K 11/0743; F16K 11/074; F16K 11/072; G01N 30/20; G01N 2030/201; G01N 2030/202; G01N 30/38; G01N 2030/382; G01N 2030/381; G01N 30/34; G01N 2030/347
See application file for complete search history.

(56) References Cited

U.S. PATENT DOCUMENTS

| | | | | |
|---|---|---|---|---|
| 734,186 | A * | 7/1903 | Mack | F16K 11/0743 137/625.43 |
| 3,630,371 | A * | 12/1971 | Hrdina | F16K 11/072 210/198.2 |
| 3,918,493 | A * | 11/1975 | Tobias | F16K 11/072 137/625.23 |
| 3,923,460 | A * | 12/1975 | Parrott | G01N 30/466 210/264 |

(Continued)

*Primary Examiner* — Reinaldo Sanchez-Medina
*Assistant Examiner* — David Colon-Morales
(74) *Attorney, Agent, or Firm* — Womble Bond Dickinson (US) LLP

(57) ABSTRACT

A blend valve assembly including a plurality of ports, a stator having at least one fluid flow path defined therein that extends between at least one port of the plurality of ports in communication with the primary fluid media and at least one port of the plurality of ports in communication with an intake of a testing device, and a rotor comprising at least one fluid flow path defined therein. The rotor is movable between a series of positions such that the blend valve assembly is operable to provide the intake of the testing device with only the primary fluid media and to provide the intake of the testing device with a blend of the primary fluid media and the secondary fluid media.

16 Claims, 6 Drawing Sheets

Normal Flow

Blending (56) References Cited

U.S. PATENT DOCUMENTS

| | | | | |
|---|---|---|---|---|
| 3,975,946 | A * | 8/1976 | Ball | G01N 30/20 73/61.56 |
| 4,059,009 | A * | 11/1977 | Ball | G01N 30/20 73/61.52 |
| 4,066,536 | A * | 1/1978 | Ball | B03B 5/62 209/1 |
| 4,300,393 | A * | 11/1981 | Stearns | G01N 30/20 73/863.11 |
| 4,444,066 | A * | 4/1984 | Ogle | G01N 30/20 73/61.56 |
| 4,506,558 | A * | 3/1985 | Bakalyar | G01N 30/20 73/863.72 |
| 4,558,845 | A | 12/1985 | Hunkapiller | |
| 4,625,569 | A * | 12/1986 | Toei | G01N 35/1097 73/863.72 |
| 4,705,627 | A * | 11/1987 | Miwa | B01D 15/1842 137/625.46 |
| 5,650,577 | A * | 7/1997 | Nagai | F16K 3/36 436/179 |
| 5,803,117 | A * | 9/1998 | Olsen | F16K 11/0743 137/625.11 |
| 6,012,488 | A * | 1/2000 | Nichols | F16K 11/0743 137/625.11 |
| 6,129,106 | A * | 10/2000 | Kornelson | G05D 11/137 137/101.19 |
| 6,958,119 | B2 * | 10/2005 | Yin | G01N 30/34 210/101 |
| 7,135,111 | B2 * | 11/2006 | Deguchi | G01N 30/20 210/198.2 |
| 7,216,528 | B2 * | 5/2007 | Gamache | F16K 7/14 137/240 |
| 7,503,203 | B2 * | 3/2009 | Gamache | F16K 11/074 137/51 |
| 8,241,013 | B2 * | 8/2012 | Moeller | F04B 7/0007 137/625.41 |
| 9,115,815 | B2 * | 8/2015 | Gerhardt | F16K 11/0743 |
| 9,146,182 | B1 * | 9/2015 | Wiederin | G01N 30/20 |
| 9,176,101 | B2 * | 11/2015 | Moeller | F16K 11/0743 |
| 9,417,219 | B2 * | 8/2016 | Choikhet | G01N 30/38 |
| 9,541,207 | B1 * | 1/2017 | Saetveit | F16K 11/0743 |
| 9,694,301 | B2 * | 7/2017 | Choikhet | G01N 30/463 |
| 9,752,691 | B1 * | 9/2017 | Saetveit | F16K 11/0743 |
| 9,945,762 | B2 * | 4/2018 | Wikfors | G01N 1/28 |
| 9,945,820 | B2 * | 4/2018 | Albrecht, Jr. | G01N 30/20 |
| 2002/0124895 | A1 * | 9/2002 | Thiele | F16K 3/08 137/625.46 |
| 2003/0098076 | A1 * | 5/2003 | Nichols | F16K 11/074 137/625.46 |
| 2005/0199299 | A1 * | 9/2005 | Schick | F16K 11/074 137/625.46 |
| 2009/0320925 | A1 * | 12/2009 | Nichols | F16K 3/08 137/1 |
| 2011/0067770 | A1 * | 3/2011 | Pederson | F16K 11/074 137/625.15 |
| 2012/0119127 | A1 * | 5/2012 | Tower | F16K 3/08 251/304 |
| 2012/0145937 | A1 * | 6/2012 | Richman | F16K 11/0743 251/304 |
| 2013/0174927 | A1 * | 7/2013 | Wan | F16K 11/02 137/625.15 |
| 2014/0061133 | A1 * | 3/2014 | Herman | G01N 30/20 210/659 |
| 2014/0191146 | A1 * | 7/2014 | Moeller | F16K 11/0743 251/304 |
| 2015/0090345 | A1 * | 4/2015 | Olovsson | F16K 11/0743 137/15.06 |
| 2015/0226712 | A1 * | 8/2015 | Jencks | F16K 11/0743 73/863.21 |
| 2016/0139094 | A1 * | 5/2016 | Hartmann | G01N 30/20 137/625.46 |
| 2016/0334031 | A1 * | 11/2016 | Shoykhet | G01N 30/32 |
| 2018/0363787 | A1 * | 12/2018 | Kubota | F16K 3/085 |

* cited by examiner

BLEND VALVE

CROSS REFERENCE TO RELATED APPLICATIONS

The present application claims the benefit of previously filed, U.S. Provisional Patent Application No. 62/454,503, filed Feb. 3, 2017.

INCORPORATION BY REFERENCE

The specification and drawings of U.S. Provisional Patent Application No. 62/454,503, filed Feb. 3, 2017, are specifically incorporated herein by reference as if set forth in their entirety.

SUMMARY

In one aspect, the present disclosure is directed to a blend valve assembly. The blend valve assembly generally includes a rotor, a stator, and a plurality of ports. At least one port of the plurality of ports is in communication with a first or primary fluid media flow (e.g., a liquid or gas flow), and at least one port of the plurality of ports is in communication with a second or secondary fluid media flow (e.g., a liquid or gas flow).

The stator can be substantially stationary with respect to the rotor, and the stator can have at least one flow path, for example, a stator path, extending between the at least one port in communication with the primary fluid media flow and at least one other port of the plurality of ports that is in communication with an inlet or intake of a testing machine, measurement apparatus, or other analysis device.

The rotor generally includes a rotor path defined therethrough. The rotor further can be movable between a series of positions to selectively place a groove or slot defined along, at the rotor path into and/or out of communication with selected ports of the plurality of ports, such that the blend valve assembly is operable to provide the intake of the testing device with only the primary fluid media and to provide the intake of the testing device with a blend of the primary fluid media and the secondary fluid media.

In a first or primary flow position, the rotor can be positioned with the rotor path in communication with the at least one port in communication with the secondary fluid media and at least one port of the plurality of ports in communication with a waste line that can be isolated from the testing machine/analysis device. At least a portion of the secondary fluid media may be received within the rotor path and fed or directed to the waste line so that the secondary fluid media is not fed to the testing machine or analysis device, and the primary fluid media and the secondary fluid media are maintained in fluid separation when the rotor is in the first or primary flow position. The rotor further can be moved or otherwise actuated to or toward a second, blending position.

In the second, blending position, the rotor path can be in communication with the at least one port of the plurality of ports that is in communication with the inlet or intake of the testing machine or analysis device and the stator path. Therefore, when the rotor is in the secondary or blending position, the primary and secondary fluids that are provided to the blend valve can be blended and directed into the testing machine or analysis device.

With the blend valve constructed according to principles of the present disclosure, the flow of fluids in the rotor path and the stator path will be non-zero or substantially continuous. As a result, when the rotor is moved between the secondary and primary positions, the stator path and the rotor path are swept such that the stator path or the rotor path do not retain a portion of the gases or fluids, e.g., the blended fluid, resulting from the valves previous position, i.e., there will be no unswept passages that retain a portion of the resulting fluids that may contaminate a testing procedure.

Further, the blend valve according to principles of the present disclosure may be used at elevated temperatures, such as, for example, temperatures up to approximately 350° C., and the blend valve also can be used at high pressures, for example, up to about 20,000 psi. However, it will be understood that the blend valve can be used at any suitable temperature or pressure, such as ambient/room temperatures and pressures, for example, temperatures greater than 350° C. and pressures greater than 20,000 psi, without departing from the scope of the present disclosure.

In contrast to the present disclosure, conventional valves, such as valves that use a solenoid valve and a diaphragm seal, generally allow fluids to remain in a passage which cannot be flushed to allow a new fluid to be used, such as, when not blending fluids. The new fluid therefore may push a prior secondary fluid media into the moving stream of the primary fluid media. Additionally, when such valves are in a position for non-blending, secondary fluid media may remain inside the portions of the valve and/or the connection. Such valves, without unswept passages, further can be limited to near ambient temperature by the magnetic solenoid coil required of such valves, and are limited to the operating pressure of solenoid valves and/or diaphragm valves, typically 100 psi or less.

Those skilled in the art will appreciate the above stated advantages and other advantages and benefits of various additional embodiments reading the following detailed description of the embodiments with reference to the below listed drawing figures.

BRIEF DESCRIPTION OF THE DRAWINGS

According to common practice, the various features of the drawings discussed below are not necessarily drawn to scale. Dimensions of various features and elements in the drawings may be expanded or reduced to more clearly illustrate the embodiments of the disclosure. Corresponding parts are designated by corresponding reference numbers throughout the drawings.

DETAILED DESCRIPTION

The present disclosure generally relates to blend valve assemblies and methods of blending fluids (e.g., liquids or gasses) for testing procedures. For the purpose of illustration and not for the purpose of limiting the scope of disclosure, the following detailed descriptions provide a blend valve assembly 10 with a plurality of ports 12, a stator 14, and a rotor 16 within various embodiments. The dimensions and orientations shown in exemplary sizes provided are examples of configurations of a blend valve and should not be limiting in any manner.

As generally shown in FIGS. 1, 2, 3A-B, 4A-B, and 5A-B, the blend valve assembly 10 of the present disclosure further generally includes a plurality of ports 12 that can be selectively placed into and out of communication with each other upon actuation and/or adjustment of the rotor 16 between various positions, for example to provide a series of fluids and blended fluids to a testing machine.

Figure 1:
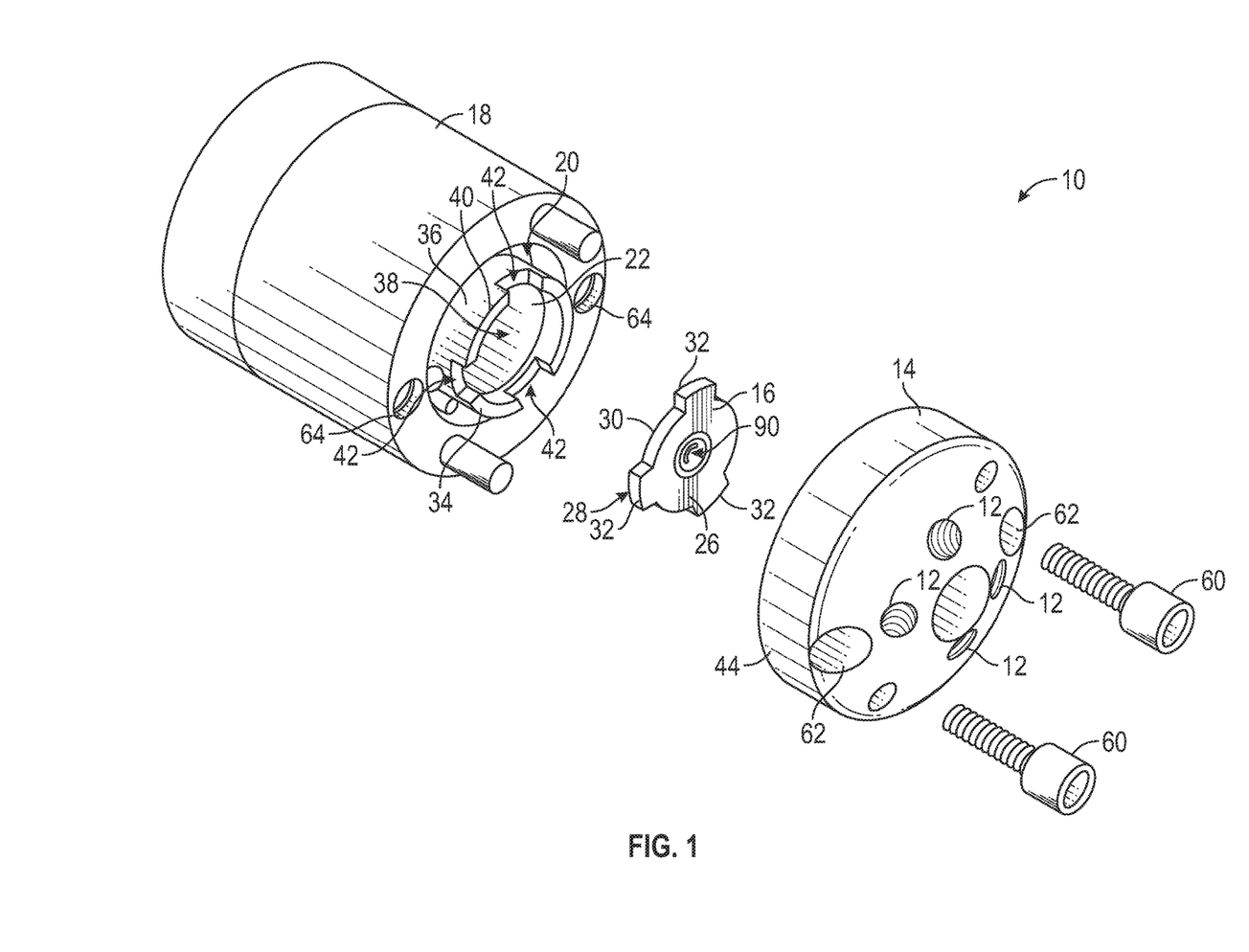
FIG. 1 shows an exploded view of a blend valve assembly according to principles of the present disclosure.

FIG. 1 shows a blend valve assembly 10 in one aspect according to principles of the present disclosure. As shown in FIG. 1, the blend valve assembly 10 includes a series of spaced ports 12, a stator 14, a rotor 16, and a valve body or housing 18. The valve body 18 generally has a cylindrical shape, though other suitable shapes, such as cubic, conical, or spherical shapes can be used without departing from the present disclosure. The valve body 18 further can be formed from any suitable material, such as a metal, a polymeric material such as plastic, and/or a composite material, without departing from the present disclosure. Metals for the valve body may include aluminum, stainless steel, or other alloys or metallic materials or combinations thereof. Plastics for the valve body may include polyether ether ketone ("PEEK"), Delrin®, or other polyoxymethylene, Ertalyte®, or other polyethylene terephthalate ("PET"), and/or other suitable plastics or polymeric materials or combinations thereof. The valve body can be formed from any material or combination of materials, however, such as a material(s) with sufficient hardness and/or stiffness to physically or dimensionally support other components of the valve assembly as defined herein, and/or cope or with local environmental conditions.

Additionally, as shown in FIG. 1, the valve body 18 includes a cavity or recess 20 defined therein and which will be configured for at least partially receiving a rotor driver 22 that is operable to move the rotor 16 between its various positions to selectively place various ones of the ports 12 into and out of communication with one another. The rotor driver 22 can include a motor, pneumatic actuator, hydraulic device, or other suitable driving device or mechanism for selectively varying the position, e.g., the angular position, of the rotor 16. The rotor driver 22 also can be in communication with a controller that can activate the rotor driver under electronic control. In addition to the rotor driver, or in the alternative, the rotor 16 can be actuated manually, such as by an operator activating a handle, knob, lever, threaded rod, or other actuation mechanism.

Figure 2:
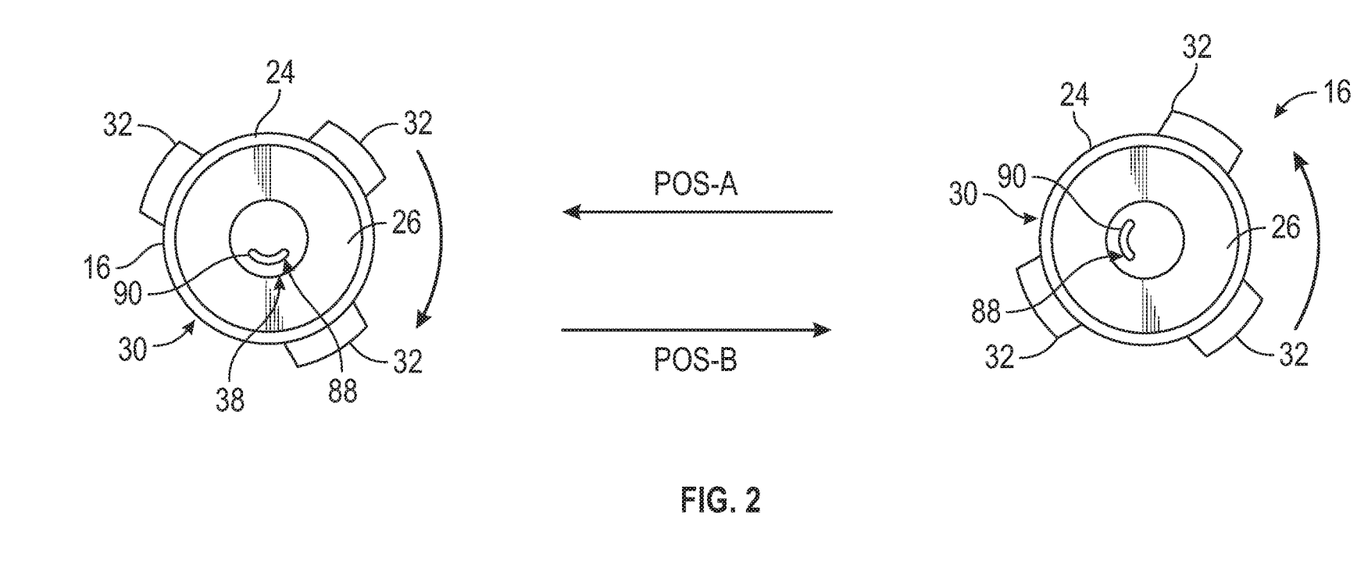
FIG. 2 shows a rotor of the blend valve assembly of FIG. 1.

FIG. 2 shows a rotor 16 according to an exemplary embodiment of the present disclosure. The rotor 16 includes a rotor body 24 that can have a circular or substantially disk-like shape, though the rotor body 24 can have any suitable shape without departing from the present disclosure. The rotor body 24 can be formed from a material such as metal, polymer, and/or composite, or any combination thereof, though other suitable materials can be used without departing from the present disclosure. In one embodiment, the rotor 24 can be made from a metal material, with a seal material, such as an elastomer or other polymeric material, adhered, bonded, fastened, or otherwise connected or applied to the metal material. Alternatively, the rotor 24 can be made from a substantially unitary polymer, such as a polyaryletherketone ("PAEK") and polytetrafluoroethylene ("PTFE") composite; a reinforced tetrafluoroethylene ("TFE") composite; polyaryletherketone; a carbon fiber reinforced, PTFE, lubricated composite, the majority of which is PTFE and carbon; a polyimide, PTFE, and/or carbon composite; virgin PTFE; Tefzel™, or other ethylene-tetrafluoresthylene ("ETFE") fluoroplastic; and/or other polymeric or composite materials or combinations thereof. Additionally, the rotor material may be selected to substantially facilitate chemical inertness for the application and for the required pressure and temperature requirements.

The rotor body 24, as shown, generally has opposing front 26 and rear 28 surfaces or faces, and a circumferential surface 30. One or more protrusions or tabs 32 may be arranged about the circumferential surface 30 of the rotor body 24. FIG. 2 shows three evenly spaced protrusion or tabs 32, but any suitable number of protrusions or tabs may be employed without departing from the scope of the present disclosure. The protrusions or tabs 32 may be operable to facilitate interengagement of the rotor 16 and a coupling 34 to connect the rotor 16 to the rotor driver 22, as described herein.

For example, as shown in FIG. 1, the coupling 34 can include a body 36 with a cavity or recess 38 that is generally sized, dimensioned, and/or configured to at least partially receive the rotor body 24. The coupling 34 further can include a sidewall 40 with one or more notches or grooves 42 configured to engage or otherwise interact with the protrusions or tabs 32 of the rotor body 24. The rotor body 24 can be at least partially received within the cavity or recess 38 of the coupling 34 such that the protrusions or tabs 32 of the rotor 16 are at least partially seated or otherwise received within the notches or grooves 42 of the coupling sidewall 40. The protrusions or tabs 32 may at least partially engage the sidewall 40 of the coupling 34 in a frictional or snap-fit arrangement to connect the rotor 16 and the coupling 34.

Figure 3A:
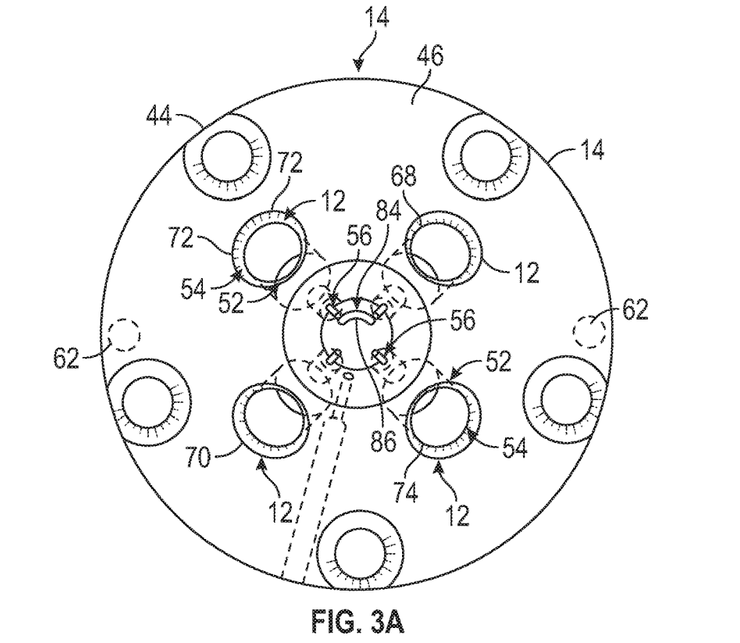
FIGS. 3A, 3B, and 3C respectively show front, side, and rear views of a stator of the blend valve assembly of FIG. 1.
Figure 3B:
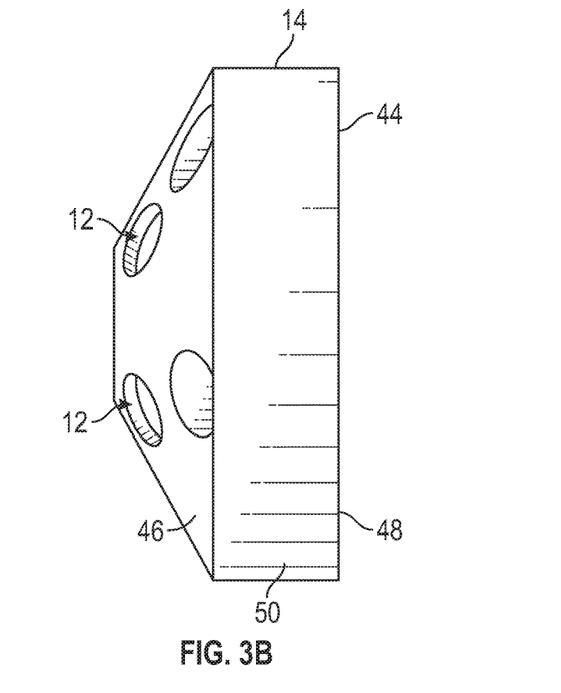
Figure 3C:
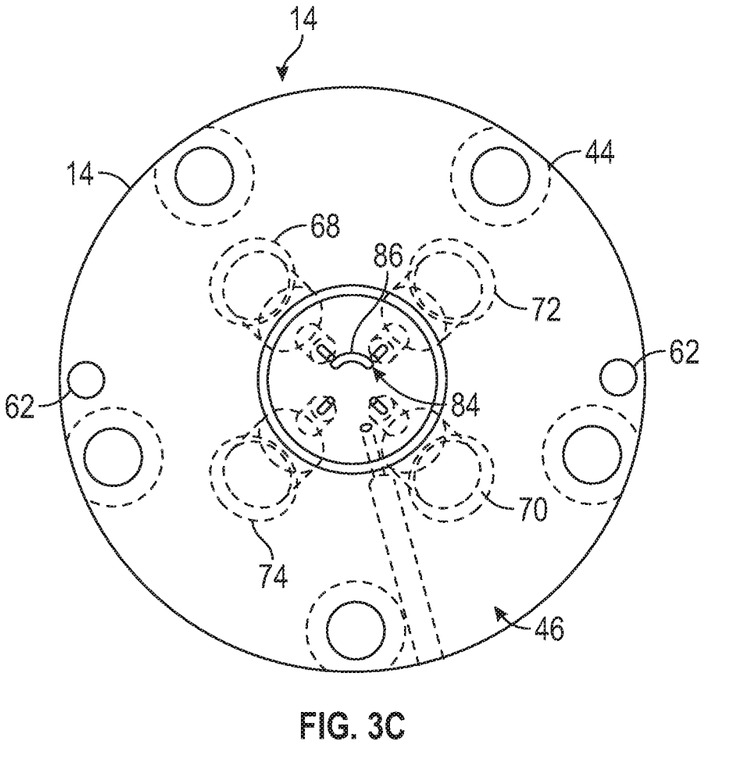

FIGS. 3A, 3B, and 3C show a stator 14 according to principles of the present disclosure. The stator 14 generally comprises a stator body 44 that includes a generally frusto-conical or conical shape, though other suitable shapes, such as polygonal, cubic, pyramidal, or hemi-spherical shapes, can be used without departing from the scope of the present disclosure. The stator body 44 can be formed from any suitable material, for example, a metal, a polymer, and/or a composite without departing from the present disclosure. Metals for the stator body may include Nitronic® 60 Stainless Steel, or any suitable stainless steel, depending upon the mechanical and chemical properties suited for the selected fluids; hastelloy-C; inconel; monel nickel; and/or titanium. Plastics for the stator body may include polyether ether ketone ("PEEK"), polyaryletherketone ("PAEK"), polyphenylene sulfide ("PPS"), ertalyte or other suitable plastics, polymeric materials, or combinations thereof.

The stator body 44 further generally includes front 46, rear 48, and side surfaces 50, and the stator body 44 has a plurality of ports 12 that comprise a passage or opening 52 defined through the stator body 44. Each port 12 will have an inlet portion 54 along or substantially adjacent to the front surface 46 and an outlet portion 56 along or substantially adjacent to the rear surface 48. The inlet portion 52 can have a larger diameter that the outlet portion 56. The inlet portion 52 generally is sized to receive tubing or conduit delivering or receiving the fluid media. This may facilitate a "zero dead volume" to avoid unswept corners or crevices. The inlets further may be sized to at least partially receive tubing of various sizes, for example, tubing of about $\frac{1}{32}$ inch, $\frac{1}{16}$ inch, $\frac{1}{8}$ inch, or $\frac{1}{4}$ inch outside diameter tubing or conduit. At least a portion of the passages in the ports may substantially match an internal diameter of the tubing or conduit. The valve ports 12 further may have one or more threaded portions operable to interact with one or more corresponding threaded portions of the tubing/conduit to secure the tubing/conduit within each respective port 12. Alternatively, it is possible to affix the tubing/conduit directly to stator, such as by welding, soldering, or smelting.

Additionally, as generally shown in FIG. 1, the stator body 44 can be coupled to the valve body 18 by fasteners 60, such as screws or bolts, received in corresponding holes or apertures 62/64 in the stator and valve bodies 44/18. With the stator body 44 coupled to the valve body 18, the rear surface 48 of the stator body 44 can at least partially engage at least a portion of the rotor 16 to substantially seal a channel or groove in the rotor 16 and/or to substantially seal a channel or groove in the stator 14, as discussed below.

Figure 4A:
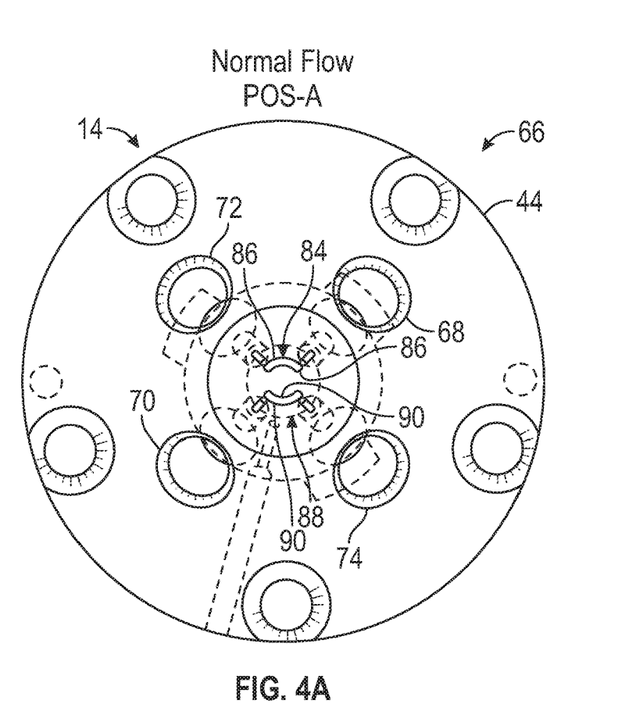
FIGS. 4A and 4B show the blend valve assembly according to FIG. 1 in a first, primary or normal flow position.
Figure 4B:
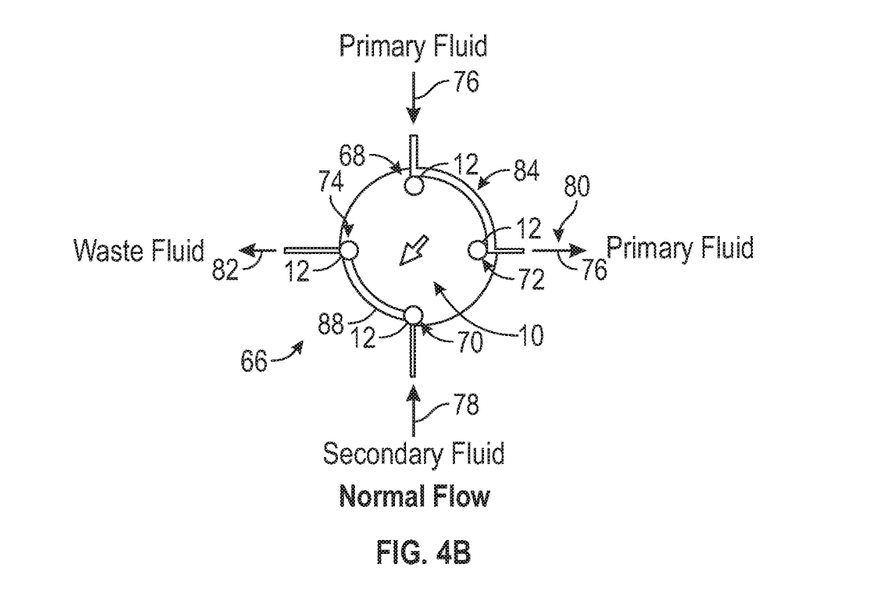
Figure 5A:
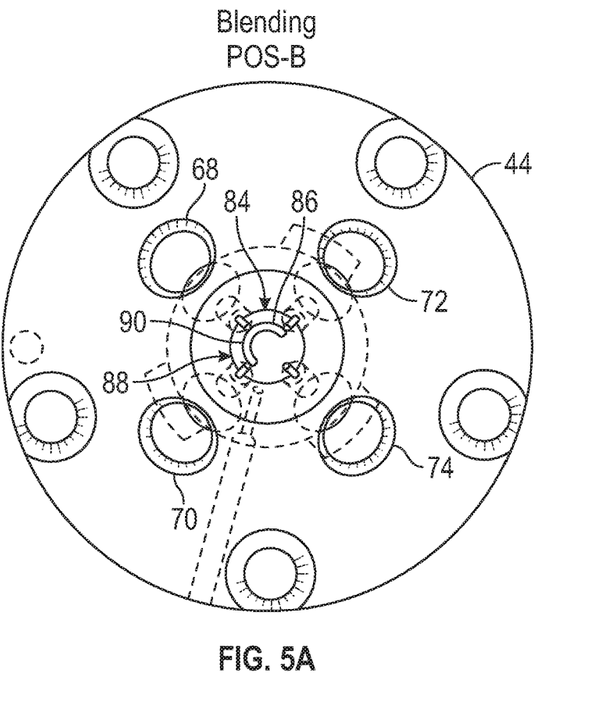
FIGS. 5A and 5B show the blend valve assembly FIG. 1 in a secondary or blending position.
Figure 5B:
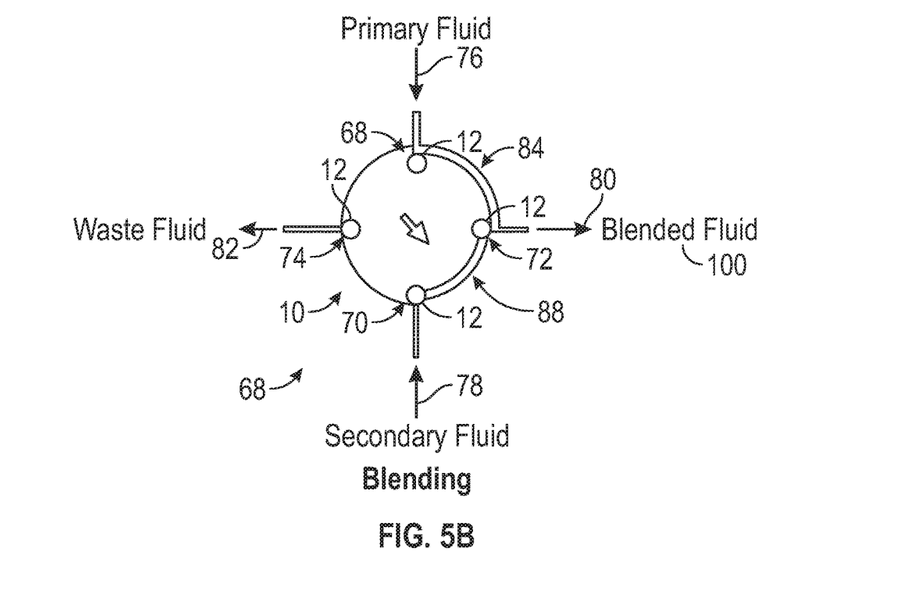

FIGS. 1, 2, 3A-C, 4A-B, and 5A-B show the blend valve assembly 10 as a four port valve, with ports 68, 70, 72, and 74 in the stator 14, and the rotor 16 is a two-position rotor that is movable between a first, normal flow position 66 (FIGS. 4A-B) and a second, blending flow position 68 (FIG. 5A-B). It will be understood, however, that the blend valve assembly can include any suitable number of values, such as 6, 8, 10, or more values, and the rotor can be movable to any suitable number of positions, such as three, four, five, or more positions.

As further shown in FIGS. 4B and 5B, port 68 of the plurality of ports 12 is in communication with a first or primary fluid media 76. Port 70 of the plurality of ports 12 is in communication with a second or secondary fluid media 78. Port 72 of the plurality of ports 12 is in communication with an inlet or intake 80 of a testing machine or analysis device and directs fluids or gases from the blend valve assembly 10 into the testing machine/analysis device. Port 74 of the plurality of ports 12 is in communication with a waste line 82. The waste line 82 is generally directed to a vessel or drain for liquid applications, or, in gas systems, the waste line 82 can be directed to an exhaust port and vented, for example, to a room, to a fume hood, or to a filter/scrubber depending on the gas or vapor used, e.g., if a noxious gas is used. The fluids/gases further may be directed to one or more receptacles or other suitable storage vessels so the fluids/gases can be recovered and/or reused.

FIGS. 3A, 3C, 4A-B, and 5A-B additionally show the stator 14 having at least one flow path, for example, a stator path 84, extending between ports 68 and 72. The stator path 84 is generally a fixed path, e.g., the primary fluid media 76 generally continuously flows along the stator path 84 and between ports 68 and 72 so that the primary fluid media 76 is provided to the intake 80 of the testing device/analysis machine. The stator path 84 can include any suitable fluid passage in the stator body 44 that allows for fluid media flow therethrough. In one example, shown in FIG. 5A, the stator path 84 can include a groove or slot 86 defined in the rear surface 48 of the stator body 44. The groove or slot 86 can be at least partially in communication with the outlets of ports 68 and 72. With the stator body 44 connected to the valve body 18, the front surface 26 of the rotor body 24 may at least partially seal or at least partially enclose the groove or slot 86. The primary fluid media 76 thus can be directed to the testing machine with a substantially non-zero flow rate or a substantially continuous flow along the stator path 84.

FIGS. 2, 4A-B, and 5A-B show that the rotor 16 further can include at least one flow path defined therein, for example, a rotor path as indicated by 88 can extend along a portion of the rotor body 24, though the rotor path 88 can include any suitable fluid passage defined in the rotor body 24 that allows for fluid media flow through the rotor. In one example, as shown in FIG. 2, the rotor path 88 can include a groove or slot 90 defined in the front surface 26 of the rotor body 24. With the stator body 44 connected to the valve body 18, the rear surface 48 of the stator body 44 may at least partially seal or at least partially enclose the groove or slot 90. The rotor 16 is rotatable or otherwise movable, for example, under actuation of rotor driver 22, so that the groove or slot 90 can be at least partially in communication with the outlets of ports 70 and 74, with the rotor 16 in the normal flow position 66 (FIGS. 4A and 5A), and the groove or slot 90 can be at least partially in communication with the outlets of ports 70 and 72, with the rotor 16 in the blending flow position 68 (FIGS. 4B and 5B).

In the normal flow position 66, as generally shown in FIG. 4B, the blend valve assembly 10 allows the primary fluid media 76 to enter the valve at port 68. The primary fluid media 76 passes through port 68 and into the stator path 84, and exits the stator path 84 at port 72. The primary fluid media 76 further will be directed from port 72 to the testing machine/analysis device. Additionally, the secondary fluid media 78 enters the valve at port 70, and passes through the rotor path 88 to port 74 where the secondary fluid media 78 exits the valve 10 and is directed to the waste line 82. As a result, with the rotor 16 in the first, normal flow position 66, only the primary fluid media 76 is directed to the testing machine/analysis device.

As shown in FIGS. 5A and 5B, the rotor 16 can be rotated to a blending position to allow blending of the primary and secondary fluids 76, 78. In such a blending position, the valve assembly 10 allows the primary fluid media 76 to enter the valve at port 68, and passes through the stator path 84 to port 72. The secondary fluid media 78 enters the blend valve assembly 10 at port 70, and passes through rotor path 88 and meets the primary fluid media at port 72 where it becomes blended to form a blended fluid 100. With the rotor 16 in its secondary, blending position 68, the port 82 leading to waste line typically receives no fluid. That is, the rotor path 88 is actuated to be in communication with port 70 and port 72, and the blended fluid 100 containing at least a portion of the primary fluid media 76 and at least a portion of the secondary fluid media 78 is substantially directed or otherwise provided to the testing machine or analysis device.

After the blended fluid 100 is no longer required by the measurement apparatus/analysis system, the rotor 16 can be caused, for example, by movement of or otherwise activating the rotor driver 22, to rotate back to the normal flow position 66. One or both fluids 76, 78 can be changed such that other fluids, for example, flows of third and fourth fluids or other media, can be provided to the valve 10. With the rotor 16 in the normal flow position 66, the new or additional fluids flowing into or through ports 70 or 68 may flush the prior fluids, residue, or particles, e.g., substantially all trace media, etc., left by the prior fluids, from the groove or slots 86, 90 in the stator 14 and/or rotor 16, e.g., the stator path 84 and the rotor path 88. Therefore, when blending is again required, the new blend contains substantially no parts of the prior fluids, and thus will be of the required purity for subsequent use in the measurement apparatus or analysis system. In other words, as the rotor path 88 and stator path 84 generally can include a substantially consistent non-zero fluid flow, so that fluids within the rotor path 88 and stator path 84 generally will be evacuated to an extent that traces of prior fluids are substantially removed from the paths.

According to embodiments of the present disclosure, a method for blending fluids may comprise providing a primary fluid to a valve assembly, and providing a secondary fluid to the valve assembly. The method may also include directing the primary fluid to a testing or analysis machine/device through a stationary flow path defined in a stator of the valve assembly, and directing the secondary fluid to a waste path through a movable flow path defined in a rotor of the valve assembly. Additionally, the method may include moving the rotor such that the rotor path is at least partially in communication with the stator path, and blending the primary fluid and the secondary fluid to provide a blended fluid. Thereafter, the method includes providing or directing the blended fluid to the testing or analysis machine.

The foregoing description of the disclosure illustrates and describes various exemplary embodiments. Various additions, modifications, changes, etc. could be made to the exemplary embodiment without departing from the spirit and scope of the claims. It is intended that all matter named in the above description or shown in the accompanying drawings shall be interpreted as illustrative and not in a limiting sense. Additionally, the disclosure shows and describes only select embodiments in the disclosure, but the disclosure is capable of use in various other combinations, modifications, and environments and is capable of changes or modifications within the scope of the invented concept as expressed herein, commensurate with the above teachings, and/or within the skill or knowledge of the relevant art. Furthermore, certain features and characteristics of each embodiment may be selectively interchanged and applied to other illustrated and non-illustrated embodiments of disclosure.

What is claimed is:

1. A blend valve assembly for a testing or measurement device, comprising:
    a plurality of ports comprising at least one port in communication with a primary fluid media, at least one port in communication with a secondary fluid media, at least one port in communication with an intake of the testing or measurement device, and at least one port in communication with a waste line;
    a stator comprising a stator body with at least one fluid flow path defined therein that extends between the at least one port in communication with the primary fluid media and the at least one port in communication with the intake of the testing or measurement device; and
    a rotor comprising a rotor body having at least one fluid flow path defined therein, wherein the rotor is movable between a series of positions to selectively place the at least one flow path defined in the rotor into and out of communication with selected ports of the plurality of ports,
    wherein the series of positions includes a blending position in which the at least one flow path defined through the rotor is in communication with the at least one port in communication with the intake of the testing or measurement device and the at least one fluid flow path defined in the stator to blend the primary fluid media and the secondary fluid media and provide a blended fluid media directed to the intake of the testing or measurement device, and
    wherein the series of positions includes a normal flow position in which the at least one flow path defined in the rotor is in communication with the at least one port in communication with the secondary fluid media and the at least one port in communication with the waste line, and a substantially continuous flow of the secondary fluid media is provided through the at least one flow path defined in the rotor and to the waste line and a substantially continuous flow of the primary fluid media is provided through the at least one fluid flow path defined in the stator and to the intake of the testing or measurement so that the at least one flow path defined in the rotor and the at least one fluid flow path defined in the stator are substantially swept of the blended fluid media.

2. The blend valve assembly of claim 1, wherein the at least one fluid flow path defined in the stator body comprises a groove at least partially defined in at least one surface of the stator body.

3. The blend valve assembly of claim 2, wherein the plurality of ports are defined at least partially through the stator body, and wherein the at least one port in communication with the primary fluid media comprises an outlet in fluid communication with the groove defined in the at least one surface of the stator body and the at least one port in communication with the intake of the testing or measurement device comprises an inlet in fluid communication with the groove defined in the at least one surface of the stator body.

4. The blend valve assembly of claim 1, wherein rotor body comprises at least one surface positioned substantially adjacent to that the at least one surface of the stator body, and wherein the at least one fluid flow path defined in the rotor comprises a groove defined in the at least one surface of the rotor body.

5. The blend valve assembly of claim 1, further comprising a valve body comprising a chamber; and at least one drive mechanism for driving movement of the rotor disposed at least partially within the chamber of the valve body.

6. The blend valve assembly of claim 5, further comprising a coupling connected to the at least one drive mechanism for connecting the rotor body to the at least one drive mechanism.

7. The blend valve assembly of claim 6, wherein the rotor body comprises one or more tabs configured to be at least partially received within one or more corresponding notches of the coupling to facilitate interengagement of the rotor and the coupling.

8. A blend valve assembly for a testing or measurement device, comprising:
    a drive mechanism;
    a valve body comprising a chamber at least partially defined therein, the chamber at least partially receiving the drive mechanism;
    a stator comprising a stator body coupled to the valve body and having a plurality of ports defined therethrough including at least one port in communication with a primary fluid media, at least one port in communication with a secondary fluid media, and at least one port in communication with an intake of the testing or measurement device; the stator further comprising a stator flow path that extends between the at least one port in communication with the primary fluid media and the at least one port in communication with the intake of the testing or measurement device to facilitate a substantially continuous flow of the primary fluid media to the intake of the testing or measurement device; and
    a rotor adjacent the stator and coupled to and driven by the drive mechanism and comprising a rotor flow path defined at least partially therein, wherein the drive mechanism causes movement of the rotor between a series of positions including a normal flow position to provide the intake of the testing or measurement device with the primary fluid media and a blending position to provide the intake of the testing or measurement device with a blended fluid media including a blend of the primary fluid media and the secondary fluid media;

wherein when the rotor is positioned in the normal flow position, there is the substantially continuous flow of the primary fluid media in the stator flow path and a substantially continuous flow of the secondary fluid media in the rotor flow path to substantially sweep the blended media from the stator flow path and the rotor flow path.

9. The blend valve assembly of claim 8, wherein in the normal flow position, the rotor is positioned so that the rotor flow path is in communication with the at least one port in communication with the secondary fluid media and at least one port of the plurality of ports in communication with a waste line, and the secondary fluid media is at least partially received within the rotor flow path and directed to the waste line so that the secondary fluid media is not received in the testing device, and wherein in the blending position, the rotor flow path is in communication with the at least one port in communication with the intake of the testing or measurement device and the stator flow path such that the primary fluid media and the secondary fluid media are blended and directed into the intake of the testing or measurement device.

10. The blend valve assembly of claim 8, wherein the stator flow path comprises a groove at least partially defined in at least one surface of the stator body.

11. The blend valve assembly of claim 10, wherein the at least one port in communication with the primary fluid media comprises an outlet in fluid communication with the groove defined in the at least one surface of the stator body, and the at least one port in communication with the intake of the testing or measurement device comprises an inlet in fluid communication with the groove defined in the at least one surface of the stator body.

12. The blend valve assembly of claim 11, wherein the rotor comprises a rotor body having at least one surface positioned substantially adjacent at least one surface of the stator body, and wherein the rotor flow path comprises a groove defined in the at least one surface of the rotor body.

13. The blend valve assembly of claim 8, further comprising a coupling connected to the at least one drive mechanism for attaching the rotor body to the at least one drive mechanism.

14. The blend valve assembly of claim 13, wherein the rotor body comprises one or more tabs configured to be at least partially received within one or more corresponding notches defined in the coupling to facilitate interengagement of the rotor body and the coupling.

15. The blend valve assembly of claim 8, wherein the stator body is fixedly attached to the valve body using one or more fasteners.

16. A method for blending primary and secondary fluids using a blend valve assembly including a rotor that is moveable between a plurality of positions, the method comprising:
providing the primary fluid and the secondary fluid to the blend valve assembly;
with the rotor in a first position of the plurality of positions, directing the primary fluid media from the blend valve assembly to a testing or measurement device through a stationary stator flow path defined in a stator of the blend valve assembly and directing the secondary fluid to a waste path through a movable rotor flow path defined in the rotor of the blend valve assembly;
actuating the rotor to a second position of the plurality of positions such that the rotor flow path is at least partially in communication with the stator flow path;
with the rotor in a second position, blending the primary fluid and the secondary fluid to provide a blended fluid and directing the blended fluid to the testing device; and
returning the rotor to the first position, wherein a substantially continuous flow of the primary fluid is directed along the stator flow path and a substantially continuous flow of the secondary fluid media is directed along the rotor flow path such that the stator and rotor flow paths are substantially swept of the blended fluid media to reduce contamination during a testing procedure with the testing or measurement device.

* * * * *